US008512750B2

(12) United States Patent
Lewis et al.

(10) Patent No.: US 8,512,750 B2
(45) Date of Patent: Aug. 20, 2013

(54) STENTS WITH DRUG-CONTAINING AMPHIPHILIC POLYMER COATING

(75) Inventors: Andrew L. Lewis, Surrey (GB); Simon W. Leppard, Surrey (GB)

(73) Assignee: Abbott Laboratories, Abbott Park, IL (US)

( * ) Notice: Subject to any disclaimer, the term of this patent is extended or adjusted under 35 U.S.C. 154(b) by 313 days.

(21) Appl. No.: 12/906,892

(22) Filed: Oct. 18, 2010

(65) Prior Publication Data
US 2011/0034995 A1 Feb. 10, 2011

Related U.S. Application Data (62) Division of application No. 10/466,144, filed as application No. PCT/GB02/00104 on Jan. 11, 2002, now Pat. No. 7,833,544.

(30) Foreign Application Priority Data

Jan. 11, 2001 (GB) .................................. 0100760.8

(51) Int. Cl.
*A61K 9/14* (2006.01)
*A61F 2/02* (2006.01)
(52) U.S. Cl.
USPC .......................................... 424/486; 424/423
(58) Field of Classification Search
None
See application file for complete search history.

(56) References Cited

U.S. PATENT DOCUMENTS

| | | | |
|---|---|---|---|
| 5,380,299 | A | 1/1995 | Fearnot et al. |
| 5,645,883 | A | 7/1997 | Russell et al. |
| 5,900,246 | A | 5/1999 | Lambert |
| 6,872,225 | B1 | 3/2005 | Rowan et al. |

FOREIGN PATENT DOCUMENTS

| | | |
|---|---|---|
| EP | 06 23354 | 11/1994 |
| EP | 09 23953 | 6/1999 |
| WO | WO 93/01221 | 1/1993 |
| WO | WO 95/03036 | 2/1995 |
| WO | WO 95/05408 | 2/1995 |
| WO | WO 98/30615 | 7/1998 |
| WO | WO 99/01118 | 1/1999 |
| WO | WO 99/08729 | 2/1999 |
| WO | WO 01/01957 | 1/2001 |
| WO | WO 00/56283 | 9/2001 |

OTHER PUBLICATIONS

International Search Report for PCT/GB 02/00104, mailed May 10, 2002, 2 pgs.
Fischell, "Polymer Coatings for Stents", Circulation 94, pp. 1494-1495 (1996).
Giessen et al., "Marked Inflammatory Sequelae to Implantation of Biodegradable and Nonbiodegradable Polymers in Porcine Coronary Arteries", Circulation 94, pp. 1690-1997 (1996).
Kalyanasundaram et al., "Environmental Effects on Vibronic Band Intensities in Pyrene Monomer Fluorescence and their Application in Studies of Micellar Systems", JACC 99 (7), 2039, (1977).
McNair et al., "Drug Delivery from Novel PC Hydrogels", Bioactive Mat. pp. 338-339 (1995).
McNair et al., "Using Hydrogel Polymers for Drug Delivery", Med. Dev. Technology, pp. 16-22 (1996).
Topol et al., "Frontiers in Interventional Cardiology", Circulation 98, pp. 1802-1820 (1998).

*Primary Examiner* — Carlos Azpuru
(74) *Attorney, Agent, or Firm* — Squire Sanders (US) LLP (57) ABSTRACT

It is provided a method for producing a drug coated intravascular stent comprising coating a stent body with a crosslinkable amphiphilic polymer.

20 Claims, 5 Drawing Sheets

Fig.3(A).
Comparison of the fluorescence spectra of pyrene in water and lauryl methacrylate (A) and water and two example polymer systems (B)

Fig.3(B).

Fig.5. Estradiol elution profile

Fig.6. Release of 17β-estradiol from stents

STENTS WITH DRUG-CONTAINING AMPHIPHILIC POLYMER COATING

CROSS-REFERENCE TO RELATED APPLICATION

This application is a divisional application of U.S. application Ser. No. 10/466,144 filed on Jan. 5, 2004 now U.S. Pat. No. 7,833,544 which is a national phase application of PCT/GB02/00104 filed on Jan. 11, 2002 which claims priority to GB0100760.8 filed on Jan. 11, 2001, the teaching of which is incorporated herein by reference in entirety.

DESCRIPTION

The present invention relates to the delivery of drugs from stents coated with polymer. In particular the invention relates to delivery of for inhibition of restenosis following stent implantation in the treatment of cardiovascular disease.

A leading cause of mortality within the developed world is cardiovascular disease. Coronary disease is of most concern. Patients having such disease usually have narrowing in one or more coronary arteries. One treatment is coronary stenting, which involves the placement of a stent at the site of acute artery closure. This type of surgery has proved effective in restoring vessel patency and decreasing myocardial ischemia. However the exposure of currently used metallic stents to flowing blood can result in thrombus formation, smooth muscle cell proliferation and acute thrombotic occlusion of the stent.

Non-thrombogenic and anti-thrombogenic coatings for stents have been developed. One type of balloon expandable stent has been coated with polymers having pendant zwitterionic groups, specifically phosphorylcholine (PC) groups, generally described in WO-A-93/01221. A particularly successful embodiment of those polymers suitable for use on balloon expandable stents has been described in WO-A-98/30615. The polymers coated onto the stent have pendant crosslinkable groups which are subsequently crosslinked by exposure to suitable conditions, generally heat and/or moisture. Specifically a trialkoxysilylalkyl group reacts with pendant groups of the same type and/or with hydroxyalkyl groups to generate intermolecular crosslinks. The coatings lead to reduced thrombogenicity.

Fischell, T. A. in Circulation (1996) 94: 1494-1495 describes tests carried out on various polymer coated stents. A thinner uniform polyurethane coating, having a thickness of 23 μm was observed to have a better performance than a relatively non uniform thicker layer having a thickness in the range 75 to 125 μm. The thicker coatings are further described by Van der Giessen, W. J. et al., in Circulation: 1996:94:1690-1997.

It has been suggested to utilise coatings on stents as reservoirs for pharmaceutically active agents desired for local delivery.

In U.S. Pat. No. 5,380,299 a stent is provided with a coating of a thrombolytic compound and optionally an outer layer of an anti-thrombotic compound. The stent may be precoated with a "primer" such as a cellulose ester or nitrate.

Other drug containing stents and stent coatings are described by Topol and Serruys in Circulation (1998) 98:1802-1820.

McNair et al., in Proceedings of the International Symposium on Controlled Release Bioactive Materials (1995) 338-339 describe in vitro investigations of release of three model drugs, caffeine, dicloxacillin and vitamin B12, from hydrogel polymers having pendant phosphorylcholine groups. Alteration of the hydrophilic/hydrophobic ratio of the (hydrophilic) phosphorylcholine monomer 2-methacryloyloxyethyl phosphorylcholine, (HEMA-PC) and a hydrophobic comonomer and crosslinking of the polymer allows preparation of polymers having water contents when swollen in the range 45 to 70 wt %. Crosslinking is achieved by incorporating a reactive monomer 3-chloro-2-hydroxypropylmethacrylate. The tests are carried out on membranes swollen in aqueous drug solutions at 37° C. The release rates of the model drugs are influenced by the molecular size, solute partitioning and degree of swelling of the polymer. Dicloxacillin is found to have a higher half life for release than its molecular size would indicate, and the release profile did not appear to be Fickian.

McNair et al, in Medical Device Technology, December 1996, 16-22, describe three series of experiments. In one, polymers formed of HEMA-PC and lauryl methacrylate crosslinked after coating by unspecified means are cocoated with drugs onto stents. Release rates of dexamethasone from the stent, apparently into an aqueous surrounding environment, was determined. Drug release from cast membranes, as model coatings, showed that the release rate obeyed Fickian diffusion principles, for hydrophilic solutes. In the third series of tests, a non-crosslinked polymer coating, free of drug, coated on a stent, had a significant decrease in platelet adhesion when coated on a stent used in an ex-vivo arteriovenous shunt experiment. The stent coating method was not described in detail.

Stratford et al. in "Novel phosphorylcholine based hydrogel polymers:developments in medical device coatings" describe polymers formed from 2-methacryloyloxyethyl phosphorylcholine, a higher alkyl methacrylate, hydroxypropylmethacrylate and a methacrylate ester comonomer having a reactive pendant group. These PC polymers were investigated to determine the feasibility of delivering drugs and model drugs. Results are shown for caffeine, dicloxacillin, vitamin B12, rhodamine and dipyridamole. The device on which the drug is coated is a guidewire that is, it is not an implant.

In EP-A-0623354, solutions of drug and polymer in a solvent were used to coat Wiktor type tantalum wire stents expanded on a 3.5 mm angioplasty balloon. The coating weights per stent were in the range 0.6 to 1.5 mg. Coating was either by dipping the stent in the solution, or by spraying the stent from an airbrush. In each case coating involved multiple coating steps. The drug was for delivery to the vessel wall. The drugs suggested as being useful for delivery from stents were glucocorticoids, antiplatelet agents, anticoagulants, antimitotic agents, antioxidants, antimetabolite agents and antiinflammatory agents. The worked examples all use dexamethasone delivered from a bioabsorbable polymer.

In U.S. Pat. No. 5,900,246 drugs are delivered from a polyurethane coated substrate such as a stent. The polyurethanes may be modified to control its compatibility with lipophilic or hydrophilic drugs. Suitable drugs are antithrombotic agents, antiinflammatory agents such as steroids, antioxidants, antiproliferative compounds and vasodilators. Particularly preferred drugs are lipophilic compounds. A polyurethane coated stent is contacted with a drug in a solvent which swells the polyurethane, whereby drug is absorbed into the polyurethane. Selection of a suitable solvent took into account the swellability of the polyurethane and the solubility of the drug in the solvent. It was observed that lipophilic drugs loaded in this way released more slowly from hydrophobic polymer than more hydrophilic drugs, by virtue of interaction of the lipophilic drug with hydrophobic polymer.

In EP-A-0923953 coatings for implantable devices, generally stents, comprise an undercoat comprising particulate drug and polymer matrix, and an overlying topcoat which partially covers the undercoat. The top coat must be discontinuous in situ, in order to allow release of the drug from the undercoat. Examples of drugs include antiproliferatives, steroidal and non steroidal antiinflammatories, agents that inhibit hyperplasia, in particular restenosis, smooth muscle cell inhibitors, growth factor inhibitors and cell adhesion promoters. The worked examples use heparin and dexamethasone. The polymer of the undercoat is, for example, hydrophobic biostable elastomeric material such as silicones, polyurethanes, ethylene vinyl acetate copolymers, polyolefin elastomers, polyamide elastomers and EPDM rubbers. The top layer is suitably formed of non-porous polymer such as fluorosilicones, polyethylene glycols, polysaccharides and phospholipids. In the examples, the undercoat comprised silicone polymer, and coating with the polymer/drug mixture was carried out by spraying a suspension in which both drug and polymer were dispersed, followed by curing of the polymer.

In our earlier specification WO-A-0101957, unpublished at the priority date hereof, we describe methods for loading drugs into polymer coated stents. The polymer coating preferably comprised a crosslinked copolymer of an ethylenically unsaturated zwitterionic monomer with a hydrophobic comonomer. The drug was intended to be delivered into the wall of the vessel in which the stent was implanted and the thickness of the coating on the stent was adapted so as to provide higher drug dosage on the outer surface of the stent. The drugs were selected from antiproliferatives, anticoagulants, vasodilators, antiinflammatories, cytotoxic agents and antiangiogenic compounds.

It is well known to those who work in the area of surfactant chemistry that it is possible to determine critical micelle concentrations by use of hydrophobic probes, which seek out the hydrophobic interior of micelles in preference to remaining in an aqueous environment. Pyrene is one such molecule. Moreover, the fluorescence intensities of various vibronic fine structures in the pyrene molecules' fluorescence spectrum shows strong environmental effects based upon the polarity of the solvent in which it is present (Kalyanasundaram, K et al.; *JACC*, 99(7), 2039, 1977). The ratio of the intensity of a pair of characteristic bands (I3:I1) is relevant to the environment. A value for I3:I1 of about 0.63 is indicative of an aqueous environment whilst a value of about 1 is indicative of a hydrophobic environment.

In WO-A-95/03036 it is suggested that stents are coated with antiangiogenic drugs to inhibit tumour invasion. Many of the drugs are sparingly water soluble. The antiangiogenic agent is delivered from a polymeric carrier, such as a bioerodable or biodegradable polymer.

In WO-A-00/56283, polymers having metal chelating activities are said to have matrix metalloproteinase (MMP) inhibitory activity. The polymers may be coated onto a stent. It is suggested that MMP's contribute to the development of atherosclerotic plaques and post angioplasty restenotic plaques. The MMP inhibiting activity of the polymers is believed to be useful in inhibiting restenosis. The polymers may be coated onto a stent and may have additional pharmaceutically active agents dispersed therein, some of which may be sparingly soluble in water. Polymers having matrix metalloproteinase inhibitory (MMPI) activity are capable of chelating divalent metals, and are generally polymers of unsaturated carboxylic acids although sulphonated anionic hydrogels may be used. One example of a monomer for forming a sulphonated anionic hydrogel is N,N-dimethyl-N-methacryloyloxyethyl-N-(3-sulphopropyl) ammonium betaine. Other examples of polymers are acrylic acid based polymers modified with $C_{10-30}$-alkyl acrylates crosslinked with di- or higher-functional ethylenically unsaturated crosslinking agents. There is no specific suggestion of how to provide a coating on a stent comprising both MMPI active polymer and additional therapeutic agent.

In WO-A-99/01118, antioxidants are combined with antineoplastic drugs to improve their cytotoxicity. One utility of the antineoplastic combination is in the treatment of vascular disease. The drug combination may be administered from a controlled release system.

The crosslinkable polymer of 2-methacryloyloxyethyl-2'-trimethyl ammoniumethylphosphate inner salt and dodecyl methacrylate with s crosslinking monomer, coated onto a stent and cured, has been shown to reduce restenosis following stent delivery for the treatment of atherosclerotic conditions. In PCT/GB00/02087 mentioned above, we show that a range of drugs may be loaded onto the polymer coated stents such that delivery of the drug into adjacent tissue takes place.

The present invention relates to a stent having a polymer coating, and comprising a sparingly water soluble drug which may be delivered over an extended period of time from the stents after placement.

A new intravascular stent comprises a metal body having a coating comprising polymer and at least 20 μg per stent of a restenosis inhibiting agent in which the restenosis inhibiting agent is a sparingly water soluble drug and the polymer in the coating is a cross-linked amphiphilic polymer which, when swollen with water containing pyrene, has hydrophobic domains observable by pyrene fluorescence having an intensity ratio I3:I1 of at least 0.8.

The agent should be present on the external wall of the stent at a concentration of at least about 0.05 $μg/mm^2$, the area being based on the surface area of metal.

The ratio of I3:I1 is preferably about 1.

The drug should preferably have a water solubility of less than 1 mg/mg at room temperature and a logP, where P is the partition coefficient between octanol and water, of at least 1.5, preferably at least 2 or more.

Preferably, on at least the outer wall of the stent the, coating comprises a layer of the said amphiphilic polymer in which the drug is absorbed. Additionally there may be drug absorbed into polymer in the coating on the inner wall.

It may be possible to provide a sufficiently high does of drug on the stent in form of absorbed material. However, sometimes it may be desirable to provide higher doses than may be loaded into the amphiphilic polymer matrix. For instance, it may be undesirable to increase the level of polymer on the stent so as to be able to support a higher loading of drug. In a preferred stent, the coating on the outer wall of the stent comprises an inner layer of the said amphiphilic polymer, and adhered to said inner layer, crystalline drug. Provision of crystalline drug may also confer useful release characteristics on the stent. The crystalline material may be controlled of a particle size, for instance, to confer desired release characteristics which complement the release of absorbed drug from the polymer coating.

In a preferred embodiment of the invention, the coating on at least the outer wall of the stent comprises an inner layer of the said amphiphilic polymer and the top coat comprising a non-biodegradable, biocompatible semipermeable polymer. The semipermeable polymer is selected so as to allow permeation of drug through the top layer when the stent is in an aqueous environment. In such an environment, the semipermeable polymer may, for instance, be swollen, and it is in this form that it should allow permeation of the active drug. A topcoat may confer desirable controlled release characteristics. Its use of particular value for the preferred embodiment where coating comprises crystalline drug adhered to an inner layer of amphiphilic polymer. The topcoat in such an embodiment has several functions. It provides a smooth outer profile, minimises loss of drug during delivery, provides a biocompatible interface with the blood vessel after implantation and controls release of drug from the stent into the surrounding tissue in use.

A topcoat is preferably substantially free of drug prior to implantation of the stent.

A topcoat is preferably formed of a cross-linked amphiphilic polymer. The coating may be cross-linked or linear. Preferably it is the same as the first amphiphilic polymer.

In the present invention, an amphiphilic polymer comprises groups conferring hydrophilicity and groups conferring hydrophobicity. Preferably the groups conferring hydrophilicity comprise zwitterionic groups.

Preferably the groups conferring hydrophobicity comprise pendant hydrophobic groups selected from $C_{4-24}$-alkyl, -alkenyl and -alkynyl groups any of which may be substituted by one or more fluorine atoms, aryl, $C_{7-24}$ aralkyl, oligo ($C_{3-4}$ alkoxy) alkyl and siloxane groups.

Most preferably the polymer is formed from ethylenically unsaturated monomers including a zwitterionic monomer and a hydrophobic comonomer. For forming a crosslinkable polymer, the ethylenically unsaturated monomers preferably include one or more reactive monomer having a pendant reactive group(s) capable of forming intermolecular crosslinks.

Preferably the zwitterionic monomer has the general formula I:

$$YBX \qquad \qquad I$$

wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from $CH_2\!=\!C(R)CH_2O\!-\!$, $CH_2\!=\!C(R)CH_2OC(O)\!-\!$, $CH_2\!=\!C(R)OC(O)\!-\!$, $CH_2\!=\!C(R)O\!-\!$, $CH_2\!=\!C(R)CH_2OC(O)N$ ($R^1$), $R^2OOCCR\!=\!CRC(O)O\!-\!$, $RCH\!=\!CHC(O)O\!-\!$, $RCH\!=\!C(COOR^2)CH_2C(O)O\!-\!$, wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1-4}$ alkyl group;

K is a group —$(CH_2)_pOC(O)$—, —$(CH_2)_pC(O)O$—, —$(CH_2)_pOC(O)O$—, —$(CH_2)_pNR^3$—, —$(CH_2)_pNR^3C(O)$—, —$(CH_2)_pNR^3$—, —$(CH_2)_pNR^3C(O)O$—, —$(CH_2)_pOC(O)NR^3$—, —$(CH_2)pNR^3C(O)NR^3$— (in which the groups $R^3$ are the same or different), —$(CH_2)_pO$—, $(CH_2)_pSO_3$—, or, optionally in combination with B, a valence bond;

p is from 1 to 12; and $R^3$ is hydrogen or a $C_1$-$C_4$ alkyl group.

In group X, the atom bearing the cationic charge and the atom bearing the anionic charge are generally separated by 2 to 12 atoms, preferably 2 to 8 atoms, more preferably 3 to 6 atoms, generally including at least 2 carbon atoms.

Preferably the cationic group in zwitterionic group X is an amine group, preferably a tertiary amine or, more preferably, a quaternary ammonium group. The anionic group in X may be a carboxylate, sulphate, sulphonate, phosphonate, or more preferably, phosphate group. Preferably the zwitterionic group has a single monovalently charged anionic moiety and a single monovalently charged cationic moiety. A phosphate group is preferably in the form of a diester.

Preferably, in a pendant group X, the anion is closer to the polymer backbone than the cation.

Alternatively group X may be a betaine group (ie in which the cation is closer to the backbone), for instance a sulpho-, carboxy- or phospho-betaine. A betaine group should have no overall charge and is preferably therefore a carboxy- or sulpho-betaine. If it is a phosphobetaine the phosphate terminal group must be a diester, i.e., be esterified with an alcohol. Such groups may be represented by the general formula II $$-\!X^1\!-\!R^4\!-\!N^+(R^5)_2\!-\!R^6\!-\!V \qquad \qquad II$$

in which $X^1$ is a valence bond, —O—, —S— or —NH—, preferably —O—;

V is a carboxylate, sulphonate or phosphate (diester-monovalently charged) anion;

$R^4$ is a valence bond (together with $X^1$) or alkylene —C(O) alkylene- or —C(O)NHalkylene preferably alkylene and preferably containing from 1 to 6 carbon atoms in the alkylene chain;

the groups $R^5$ are the same or different and each is hydrogen or alkyl of 1 to 4 carbon atoms or the groups $R^5$ together with the nitrogen to which they are attached form a heterocyclic ring of 5 to 7 atoms; and $R^6$ is alkylene of 1 to 20, preferably 1 to 10, more preferably 1 to 6 carbon atoms.

One preferred sulphobetaine monomer has the formula II

II where the groups $R^7$ are the same or different and each is hydrogen or $C_{1-4}$ alkyl and d is from 2 to 4.

Preferably the groups $R^7$ are the same. It is also preferable that at least one of the groups $R^7$ is methyl, and more preferable that the groups $R^7$ are both methyl.

Preferably d is 2 or 3, more preferably 3.

Alternatively the group X may be an amino acid moiety in which the alpha carbon atom (to which an amine group and the carboxylic acid group are attached) is joined through a linker group to the backbone of polymer A. Such groups may be represented by the general formula IV

IV in which $X^2$ is a valence bond, —O—, —S— or —NH—, preferably —O—, $R^9$ is a valence bond (optionally together with $X^2$) or alkylene, —C(O)alkylene- or —C(O)NHalkylene, preferably alkylene and preferably containing from 1 to 6 carbon atoms; and the groups $R^8$ are the same or different and each is hydrogen or alkyl of 1 to 4 carbon atoms, preferably methyl, or two of the groups $R^8$, together with the nitrogen to which they are attached, form a heterocyclic ring of from 5 to 7 atoms, or the three group $R^8$ together with the nitrogen atom to which they are attached form a fused ring structure containing from 5 to 7 atoms in each ring.

X is preferably of formula V

V in which the moieties $X^3$ and $X^4$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group.

Preferably W contains as cationic group an ammonium group, more preferably a quaternary ammonium group.

The group $W^+$ may for example be a group of formula —$W^1$—$N^+R^{10}_3$—$W^1$—$P^+R^{11}_3$—$W^1$—$S^+R^{11}_2$ or —$W^1$-$Het^+$ in which:

$W^1$ is alkanediyl of 1 or more, preferably 2-6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups $R^{10}$ are the same or different and each is hydrogen or alkyl of 1 to 4 carbon atoms, preferably methyl, or aryl, such as phenyl or two of the groups $R^{10}$ together with the nitrogen atom to which they are attached form a heterocyclic ring containing from 5 to 7 atoms or the three groups $R^{10}$ together with the nitrogen atom to which they are attached form a fused ring structure containing from 5 to 7 atoms in each ring, and optionally one or more of the groups $R^{10}$ is substituted by a hydrophilic functional group, and the groups $R^{11}$ are the same or different and each is $R^{10}$ or a group $OR^{10}$, where $R^{10}$ is as defined above; or Het is an aromatic nitrogen-, phosphorus- or sulphur-, preferably nitrogen-, containing ring, for example pyridine.

Preferably $W^1$ is a straight-chain alkanediyl group, most preferably ethane-1,2 diyl.

Preferred groups X of the formula V are groups of formula VI:

VI where the groups $R^{12}$ are the same or different and each is hydrogen or $C_{1-4}$ alkyl, and e is from 1 to 4.

Preferably the groups $R^{12}$ are the same. It is also preferable that at least one of the groups $R^{12}$ is methyl, and more preferable that the groups $R^{12}$ are all methyl.

Preferably e is 2 or 3, more preferably 2.

Alternatively the ammonium phosphate ester group VIII may be replaced by a glycerol derivative of the formula VB, VC or VD defined in our earlier publication No. WO-A-93/01221.

Preferably the hydrophobic comonomer has the general formula VII $Y^1R^{13}$ VII wherein $Y^1$ is selected from $CH_2$=$C(R^{14})CH_2O$—, $CH_2$=$C(R^{14})CH_2OC(O)$—,
$CH_2$=$C(R^{14})OC(O)$—, $CH_2$=$C(R^{14})O$—, $CH_2$=$C(R^{14})$
$CH_2OC(O)N(R^{15})$—, $R^{16}OCCR^{14}$=$CR^{14}C(O)O$—,
$R^{14}CH$=$CHC(O)O$—, $R^{14}CH$=$C(COOR^{16})CH_2C(O)$—O—, wherein:
$R^{14}$ is hydrogen or a $C_1$-$C_4$ alkyl group;
$R^{15}$ is hydrogen or a $C_1$-$C_4$ alkyl group or $R^{15}$ is $R^{13}$;
$R^{16}$ is hydrogen or a $C_{1-4}$ alkyl group;
$A^1$ is —O— or —$NR^{15}$—; and $K^1$ is a group —$(CH_2)_qOC(O)$—, —$(CH_2)_qC(O)O$—, $(CH_2)_qOC(O)O$—, —$(CH_2)_qNR^{17}$—, —$(CH_2)_qNR^{17}C(O)$—, —$(CH_2)_qC(O)NR^{17}$—, $(CH_2)_qNR^{17}C(O)O$—, —$(CH_2)_qOC(O)NR^{17}$—, —$(CH_2)_qNR^{17}C(O)NR^{17}$— (in which the groups $R^{17}$ are the same or different), —$(CH_2)_qO$—, —$(CH_2)_qSO_3$—, or a valence bond p is from 1 to 12;

and $R^{17}$ is hydrogen or a $C_1$-$C_4$ alkyl group;

and $R^{13}$ is the hydrophobic group.

In the comonomer of the general formula VII, the group $R^{13}$ is preferably a hydrophobic group, preferably:

a) a straight or branched alkyl, alkoxyalkyl or oligoalkoxyalkyl chain containing 4 or more, preferably 6 to 24 carbon atoms, unsubstituted or substituted by one or more fluorine atoms optionally containing one or more carbon double or triple bonds;

b) an aryl or aralkyl, preferably phenyl, phenethyl or benzyl; or c) a siloxane group —$(CR^{18}_2)_{qq}(SiR^{19}_2)(OSiR^{19}_2)_{pp}R^{19}$ in which each group $R^{18}$ is the same or different and is hydrogen or alkyl of 1 to 4 carbon atoms, or aralkyl, for example benzyl or phenethyl, each group $R^{19}$ is alkyl of 1 to 4 carbon atoms, qq is from 1 to 6 and pp is from 0 to 49

Most preferably $R^{13}$ is a straight alkyl having 4 to 18, preferably 12 to 16 carbon atoms.

The reactive monomer to which provides crosslinkability preferably has the general formula VIII $$Y^2B^2R^{20} \qquad \text{VIII}$$

wherein $B^2$ is a straight or branched alkylene, oxaalkylene or oligooxaalkylene chain optionally containing one or more fluorine atoms up to and including perfluorinated chains, or $B^2$ is a valence bond;

$Y^2$ is an ethylenically unsaturated polymerisable group selected from $CH_2$=$C(R^{21})CH_2$—O—, $CH_2$=$C(R^{21})CH_2OC(O)$—, $CH_2$=$C(R^{21})OC(O)$—, $CH_2$=$C(R^{21})O$—, $CH_2$=$C(R^{21})CH_2OC(O)N(R^{22})$—, $R^{23}OCCR^{21}$=$CR^{21}C(O)O$—, $R^{21}H$=$CHC(O)O$—, $R^{21}H$=$C(COOR^{23})CH_2C(O)O$— where $R^{21}$ is hydrogen or $C_1$-$C_4$ alkyl;

$R^{23}$ is hydrogen, or a $C_{1-4}$-alkyl group;

$A^2$ is —O— or —$NR^{22}$—;

$R^{22}$ is hydrogen or a $C_1$-$C_4$ alkyl group or $R^{22}$ is a group $B^2R^{20}$;

$K^2$ is a group —$(CH_2)_kOC(O)$—, —$(CH)_kC(O)O$—, —$(CH_2)_kOC(O)O$—, —$(CH_2)_kNR^{22}$—, —$(CH_2)_kNR^{22}C(O)$—, —$(CH_2)_kOC(O)O$—, —$(CH_2)_kNR^{22}$—, —$(CH_2)_kNR^{22}C(O)$—, —$(CH_2)_kC(O)NR^{22}$—, —$(CH_2)_kNR^{22}C(O)O$—, —$(CH_2)_kOC(O)NR^{22}$—, —$(CH_2)_kNR^{22}C(O)NR^{22}$— (in which the groups $R^{22}$ are the same or different), —$(CH_2)_kO$—, —$(CH_2)_kSO_3$—, a valence bond and k is from 1 to 12; and $R^{20}$ is a cross-linkable group.

Group $R^{20}$ is selected so as to be reactive with itself or with a functional group in the polymer (eg in group $R^{13}$) or at a surface to be coated. The group $R^{20}$ is preferably a reactive group selected from the group consisting of ethylenically and acetylenically unsaturated group containing radicals; aldehyde groups; silane and siloxane groups containing one or more substituents selected from halogen atoms and $C_{1-4}$-alkoxy groups; hydroxyl; amino; carboxyl; epoxy; —CHOHCH$_2$Hal (in which Hal is selected from chlorine, bromine and iodine atoms); succinimido; tosylate; triflate; imidazole carbonyl amino; optionally substituted triazine groups; acetoxy; mesylate; carbonyl di(cyclo)alkyl carbodiimidoyl; isocyanate, acetoacetoxy; and oximino. Most preferably $R^{20}$ comprises a silane group containing at least one, preferably three substituents selected from halogen atoms and $C_{1-4}$-alkoxy groups, preferably containing three methoxy groups.

Preferably each of the groups Y to $Y^2$ is represented by the same type of group, most preferably each being an acrylic type group, of the formula $H_2C$=$C(R)C(O)$-A, $H_2C$=$C(R^{14})C(O)A$ or $H_2C$=$C(R^{21})C(O)$-$A^2$, respectively. Preferably the groups R, $R^{14}$ and $R^{21}$ are all the same and are preferably H or, more preferably, $CH_3$. Preferably A, $A^1$ and $A^2$ are the same and are most preferably —O—. B and $B^2$ are preferably straight chain $C_{2-6}$-alkanediyl.

Preferably the ethylenically unsaturated comonomers comprise diluent comonomers which may be used to give the polymer desired physical and mechanical properties. Particular examples of diluent comonomers include alkyl(alk)acrylate preferably containing 1 to 24 carbon atoms in the alkyl group of the ester moiety, such as methyl (alk)acrylate or dodecyl methacrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl(alk)acrylate; an alkyl(alk)acrylamide preferably containing 1 to 4 carbon atoms in the alkyl group of the amide moiety; a hydroxyalkyl(alk)acrylate preferably containing from 1 to 4 carbon atoms in the hydroxyalkyl moiety, e.g. a 2-hydroxyethyl (alk)acrylate glyceryl-monomethacrylate or polyethyleneglycol monomethacrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains is from 1 to 4 carbon atoms, e.g. sugar acrylates, methacrylates, ethacrylates, acrylamides, methacrylamides and ethacrylamides. Suitable sugars include glucose and sorbitol. Diluent comonomers include methacryloyl glucose and sorbitol methacrylate.

Further diluents which may be mentioned specifically include polymerisable alkenes, preferably of 2-4 carbon atoms, eg. ethylene, dienes such as butadiene, ethylenically unsaturated dibasic acid anhydrides such as maleic anhydride and cyano-substituted alkenes, such as acrylonitrile.

Particularly preferred diluent monomers are nonionic monomers, most preferably alkyl(alk)acrylates or hydroxyalkyl(alk)acrylates.

It is particularly desirable to include hydroxyalkyl(alk)acrylates in combination with reactive comonomers which contain reactive silyl moieties including one or more halogen or alkoxy substituent. The hydroxyalkyl group containing monomer may be considered a reactive monomer although it also acts as a diluent. Such reactive silyl groups are reactive with hydroxy groups to provide crosslinking of the polymer after coating, for instance.

A particularly preferred combination of reactive monomers is ω(trialkoxysilyl)alkyl(meth)acrylate and an ω-hydroxyalkyl(meth)acrylate.

The monomers may, in some embodiments, comprise an ionic comonomer. Suitable comonomers are disclosed in our earlier publication WO-A-9301221.

Preferably the zwitterionic monomer is used in the monomer mixture in a molar proportion of at least 1%, preferably less than 75%, more preferably in the range 5 to 50%, most preferably 10-33%. The hydrophobic comonomer is generally used in molar proportion of at least 2%, preferably at least 5% or at least 10%, more preferably in the range 15 to 99%, especially 50 to 95%, more especially 60 to 90%. The cross-linkable monomer is preferably used in a molar amount in the range 2 to 33%, preferably 3 to 20%, more preferably 5 to 10% by mole.

The zwitterionic polymer can be represented by the general formula IX:

IX in which l is 1 to 75, m is 0 to 99, n is 0 to 33 and m+n is 25 to 99, $Y^3$ to $Y^5$ are the groups derived from Y to $Y^2$, respectively, of the radical initiated addition polymerisation of the ethylenic group in Y to $Y^2$, and B and X are as defined for the general formula I,
$R^{13}$ is as defined for the general formula VII, and
$B^2$ and $R^{20}$ are as defined for the general formula VIII.

In the preferred zwitterionic polymer in which Y, $Y^1$ and $Y^2$ are each acrylic groups the polymer has the general formula X

X in which B, X, R and A are as defined for the compound of the general formula I, $R^{14}$, $A^1$ and $R^{13}$ are as defined for the general formula VII, $R^{21}$, $D^2$, $B^2$ and $R^{20}$ are as defined for the general formula VII and I, m and n are as defined for the general formula IX The polymerisation is carried out using suitable conditions as known in the art. Thus the polymerisation involves radical initiation, using thermal or redox initiators which generate free radicals and/or actinic (e.g. u.v or gamma) radiation, optionally in combination with photoinitiators and/or catalysts. The initiator is preferably used in an amount in the range 0.05 to 5% by weight based on the weight of monomer preferably an amount in the range 0.1 to 3%, most preferably in the range 0.5 to 2%. The level of initiator is generally higher where the monomer includes reactive monomer and the polymer is cross-linkable, e.g. 1 to 20%.

The molecular weight of the polymer (as coated, where the polymer is cross-linkable) is in the range $1 \times 10^4$ to $10^6$, preferably in the range $5 \times 10^4$ to $5 \times 10^5$ D.

The monomer mixture and the monomer mixture may include a non-polymerisable diluent, for instance a polymerisation solvent. Such a solvent may provide solubility and miscibility of the monomers. The solvent may be aqueous or non-aqueous. The polymer may be recovered by precipitation from the polymerisation mixture using a precipitating solvent, or recovery may involve removal of any non polymerisable diluent by evaporation, for instance.

In the present invention the term sparingly water soluble means that at room temperature the solubility of the compound in water is less than 1 ml. The restenosis inhibiting agent (drug) is preferably a compound having a log P, where P is the octanol/water partition coefficient, of at least 1.5 for instance more than 2.

The drug should have a logP of at least 1.5, preferably at least 2. When such drugs are absorbed into polymers having the hydrophobic domains, observed using the pyrene fluorescence test, interaction apparently takes place, affecting the release rate of the drug. It is believed that the hydrophobic drug will preferentially partition into the hydrophobic domains in a similar fashion to pyrene.

Preferred drugs are steroids, especially estrogens, especially estradiol (E2) and corticosteroids, especially dexamethasone (Dex) and 6α-methylprednisolone (MP). Estradiol has a logP of 4.3 and a water solubility of 0.003 mg/ml; MP has a logP of 1.42; Dex has a logP of 2.55 and a water solubility of 0.01 mg/ml. Other examples of sparingly water-soluble drugs which may be used in the invention include statins, such as simvastatin (logP 2.06), and, though less preferably lovastatin (logP 1.7) and atorvastatin (logP 1.6).

Preferably the drug should be present in an amount in the range 20 to 1000 μg, preferably at least 50 μg, more preferably in the range 100 to 400 μg, per stent.

The stent may be made of a shape memory metal, or may be elastically self-expanding, for instance, be a braided stent. However, preferably it is a balloon expandable stent. In the embodiment of the invention, in which a topcoat is provided, the topcoat may be part of a coherent coating formed over both a stent and a stent delivery device, for instance a balloon of a balloon catheter from which a balloon expandable stent is delivered. In this case, the balloon may additionally be provided with a coating comprising drug, for instance adsorbed onto parts of its exterior surface between stent struts. Such a device may be produced by loading the stent with drug after the stent has been mounted onto the delivery catheter.

According to a further aspect of the invention there is provided a new method for producing a drug coated intravascular stent comprising the steps:

a) a metallic stent body is coated on its inner and outer walls with a cross-linkable amphiphilic polymer;

b) the cross-linkable polymer is subjected to conditions under which cross-linking takes place to produce a stent coated with polymer which, when swollen with water containing pyrene, has hydrophobic domains observable by pyrene fluorescence having an intensity ratio I3:I1 of at least 0.8;

c) at least the outer coated wall of the polymer coated stent is contacted with liquid drug composition comprising a sparingly water-soluble restenosis inhibiting drug and an organic solvent in which the drug is at least partially dissolved and which is capable of swelling the cross-linked polymer of the coating, for a time sufficient to swell the polymer coating on the outer wall, to produce a wet drug-coated stent in which drug is present in an amount of at least 20 μg per stent;

d) organic solvent is evaporated from the wet stent to produce a dry drug-coated stent.

In the method of the invention, in step c), the drug may be both absorbed into the polymer and adsorbed at the process of the polymer coating whereby, upon evaporation of the solvent in step d) crystals of drug are formed which are adherent to the surface of the dry drug coated stent.

In the method of the invention, contact of the polymer coated stent with the liquid drug composition may be by dipping the stent into a body of the stent, and/or by flowing, spraying or dripping liquid composition onto the stent with immediate evaporation of solvent from the wet stent. Such steps allow good control of drug loading onto the stent, and are particularly useful for forming the crystals of drug at the surface of polymer.

Whilst the stent may be provided with drug coating in the invention prior to being mounted onto its delivery device, it is preferred, and most convenient, for the stent to be pre-mounted onto its delivery device prior to carrying out step c). By this means, it is primarily the outer wall of the stent (as opposed to the inner wall of the stent) which becomes coated with drug. Whilst this method will generally result in drug being coated onto the stent delivery section of the delivery catheter, this is, in general, not disadvantageous. In some circumstances it may be useful for the outer surface of the delivery catheter to be provided with a coating of drug, which may be delivered to adjacent tissue upon placement of the stent in use. Generally the delivery catheter is in contact with such tissue for a short period, whereby contact is not maintained for a prolonged period, and limited level of transfer of drug from the balloon take place.

The method of the invention may include a step of applying a topcoat. In such a method a further step e) is carried out:

e) to at least the outer wall of the dry drug coated stent a polymer is applied, to form a non-biodegradable biocompatible semi-permeable polymer-containing top-coat.

In this preferred embodiment, in step e) it is preferred that a liquid top-coating composition comprising polymer is coated onto at least the outer wall and is cured after coating to form the top-coat. It is desirable for the liquid coating to be sprayed onto the outer wall of the stent, as this method has been found to minimise removal of previously applied drug.

The top-coating composition, and consequently the top coat in the product, should generally be substantially free of drug. Preferably it is substantially free of other pharmaceutical actives although in certain circumstances it may be useful to cocoat a mixture of polymer and another pharmaceutically active agent.

For the embodiment of the invention where the liquid top-coating composition comprises a cross-linkable polymer of the type preferred for use to form the first amphiphilic polymer, the liquid top-coating composition comprises cross-linkable polymer and the curing step in the preferred method involves exposure of the top-coat to cross-linking conditions.

Curing of cross-linkable polymer may involve exposure to irradiation, chemical curing agents, catalysts or, more usually raised temperature and/or reduced pressure to acceptable condensation based cross-linking reactions. Drying the liquid during composition usually involves raised temperature and/or reduced pressure for a time sufficient to reduce the amount of solvent remaining on the stent to undetectable levels or levels at which it will not interfere with subsequent processing steps, or with release of the drug in use, or be toxic to a patient in whom the stent is implanted.

Where in the preferred method, the stent is preloaded onto its delivery device before being coated with drug, the top-coat is provided over both the stent and the stent delivery section of the delivery catheter. Preferably the top-coat forms a coherent film covering the entire stent delivery section. It is preferred for the device subsequently to be sterilised and to be packaged into a sterile package for storage prior to use. Sterilisation may involve γ irradiation, or application of heat, but preferably involves contact with ethylene oxide.

Where, in the preferred method, a stent is contacted with liquid drug composition whilst mounted on a delivery device, it is important to ensure that the said contact does not adversely effect the properties of the delivery catheter. For a balloon catheter, the contact must not significantly reduce the burst strength of the balloon. A preferred balloon catheter used for delivering a stent is formed of polyamide. We have established that the use of ethanol, methanol or dimethylsulfoxide (DMSO) do not damage the balloon such that burst strength are reduced to an unacceptable level. The examples of solvents and solvent mixtures include dichloromethane (DCM), mixtures of isopropanol and water and DCM/ethanol mixtures.

The solvent must be selected to allow adequate dissolution of drug, and swelling of the cross-linked polymer coating to allow absorption of drug into the body of the polymer. Drug which is absorbed into the polymer will be released over a period of time after implantation of the stent. The liquid drug composition may comprise other components, such as crystal modifiers, polymers, salts, acids, bases etc. It may be convenient to include dissolved amphiphilic, optionally crosslinkable polymer, to confer compatibility with the polymer on the stent surface. Such a polymer may be identical to that described above used in the first aspect of the invention.

According to a further aspect of the invention there is also provided an intravascular stent comprising a metal body and a coating on the metal body comprising an amphiphilic polymer and 17β-estradiol. Preferably the amphiphilic polymer has a hydrophobic domain observable by pyrene fluorescence having an intensity ratio I3:I1 of at least 0.8, preferably about 1.0. Preferably at least 20 μg estradiol is incorporated per stent.

According to a further aspect of the invention there is also provided an intravascular stent comprising a metal body and a coating on the metal body comprising an amphiphilic polymer and 6α-methylprednisolone. Preferably the amphiphilic polymer has a hydrophobic domain observable by pyrene fluorescence having an intensity ratio I3:I1 of at least 0.8, preferably about 1.0. Preferably at least 20 μg MP is incorporated per stent. Preferred embodiments of these further aspects of the invention are preferably also covered by the main aspects of the invention and comprise the preferred aspects thereof and are produced by the inventive method.

The present inventors have established that stents according to the invention confer improved quantative coronary angioplasty results when used in animals, reduced intimal hyperplasia, increased lumen diameter and excellent clinical results as compared to control polymer coated stents.

Figure 1:
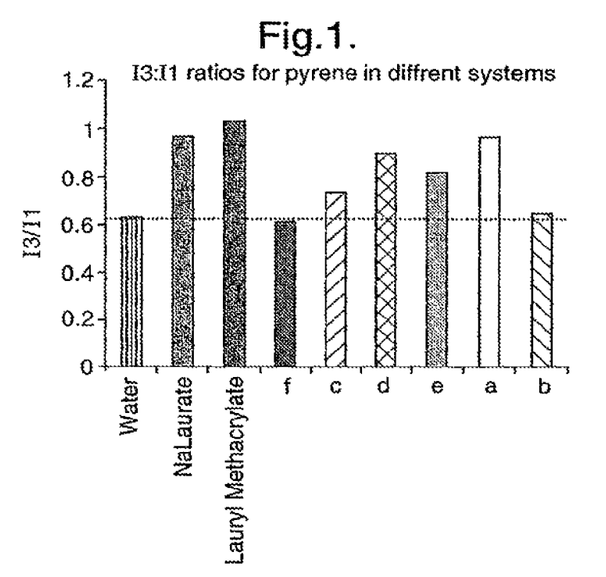
FIG. 1 shows I13:I1 ratios for pyrene in different systems.
Figure 2:
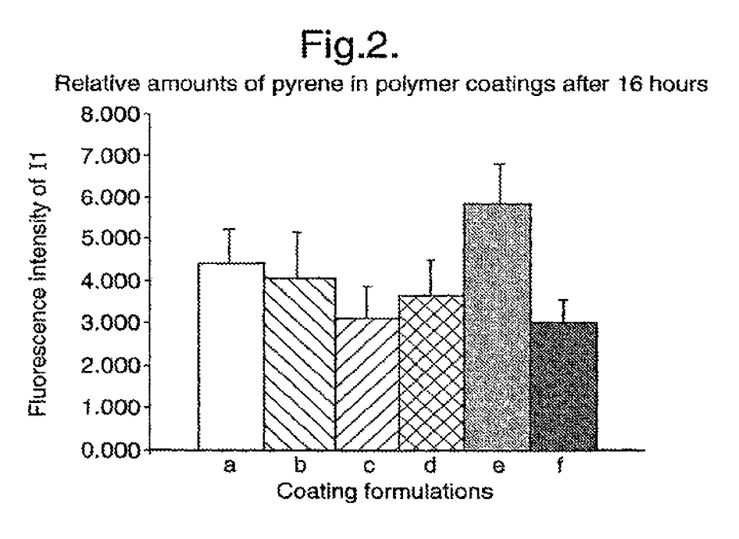
FIG. 2 shows relative amounts of pyrene in polymer coatings after 16 hours.
Figure 3A:
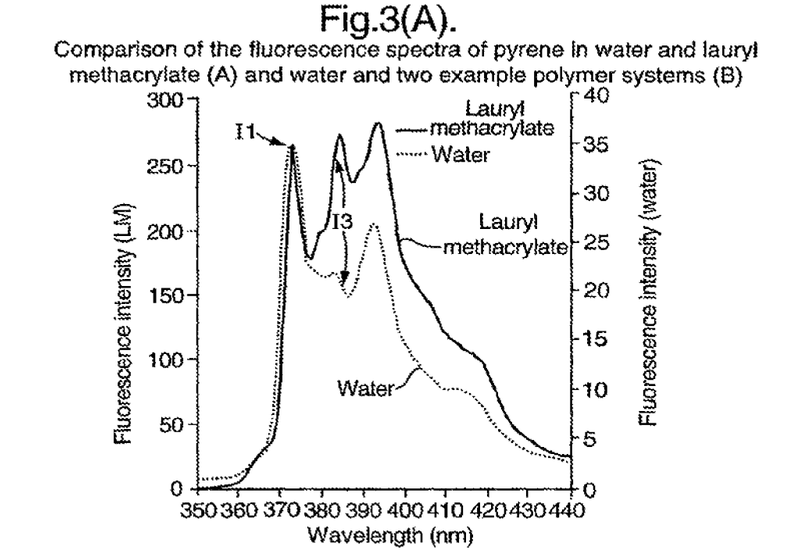
FIG. 3 shows comparison of the fluorescence spectra of pyrene in water and lauryl methacrylate (A) and water and two example polymer systems (B).
Figure 3B:
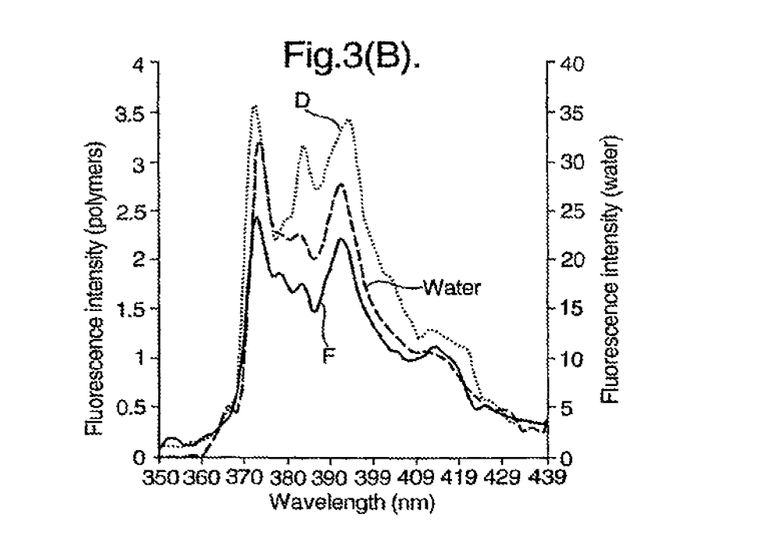

The drawings relate to the following:

FIG. 1 compares the I3:I1 ratio from the fluorescence spectra of pyrene in different environments (Ref Ex. 1);

FIG. 2 shows the amount of pyrene retained in a variety of polymer coatings as determined in Reference Example 1;

FIG. 3A compares the fluorescence spectra of pyrene in lauryl methacrylate and water;

FIG. 3B compares the fluorescence spectra of pyrene in water and in two amphiphilic polymers (Ref Ex 1)

Figure 4A:
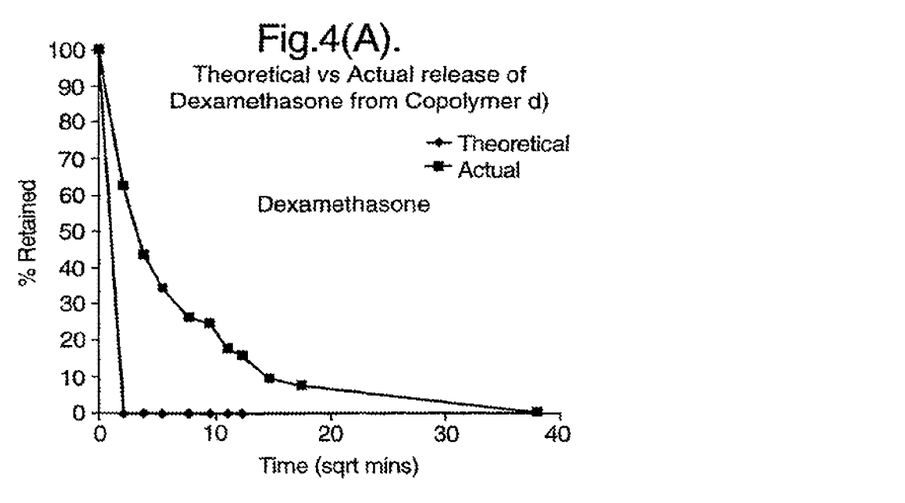
FIG. 4 shows theoretical vs. actual release of dexamethasone from copolymer d) (A) and theoretical vs. actual release of estradiol from copolymer d) (B).
Figure 4B:
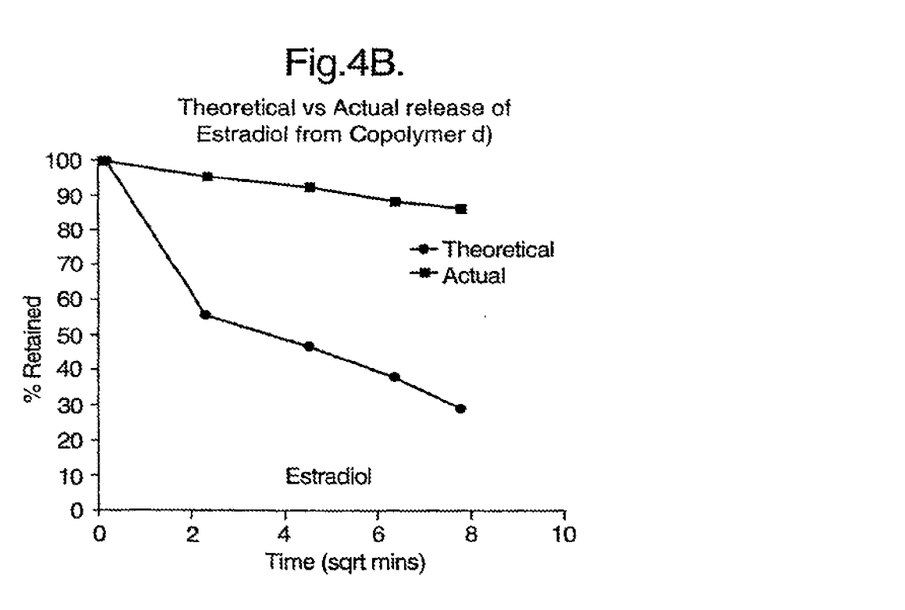

FIGS. 4a and 4b show the actual and theoretical release rates of dexamethasone and 17β-estradiol from polymers (Ref Ex 2)

Figure 5:
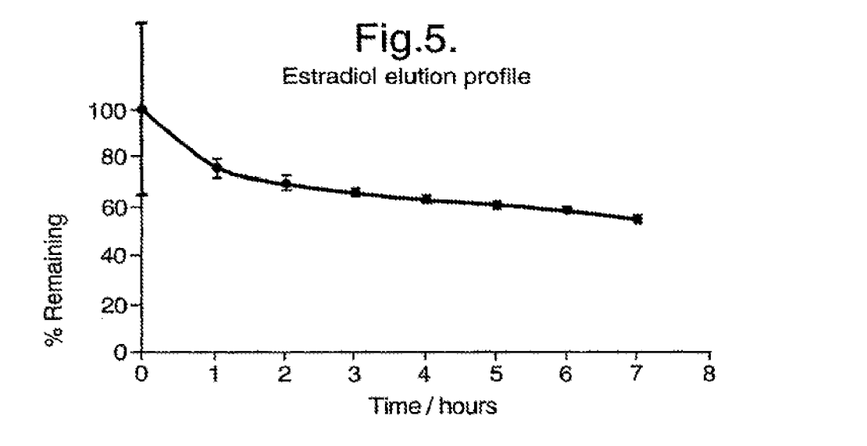
FIG. 5 shows estradiol elution profile.
Figure 6:
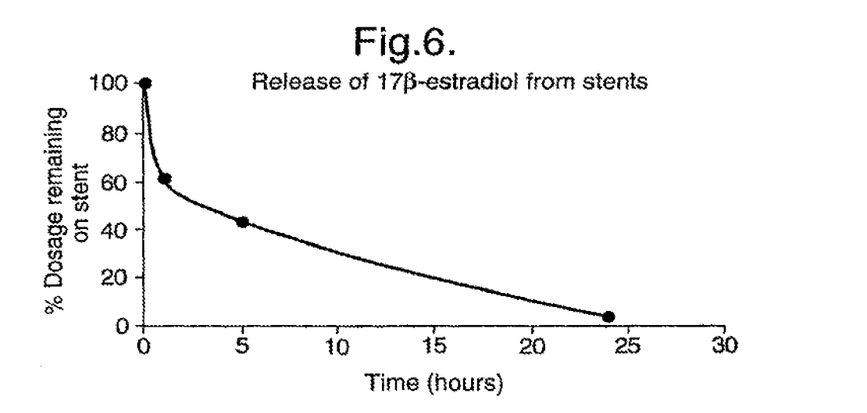
FIG. 6 shows 17 β-estradiol from stents.
Figure 7:
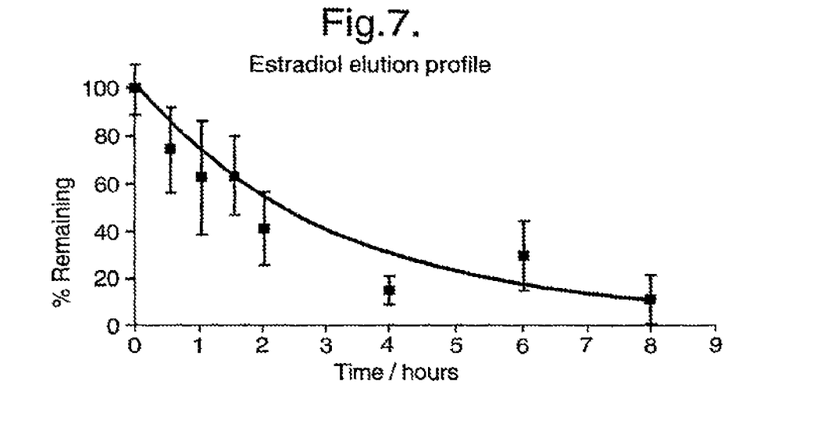
FIG. 7 shows estradiol elution profile.

FIG. 5 shows the estradiol elution profile for Example 2;

FIG. 6 shows the estradiol elution profile for Example 3;

FIG. 7 shows the estradiol elution profile for Example 4; and

Figure 8:
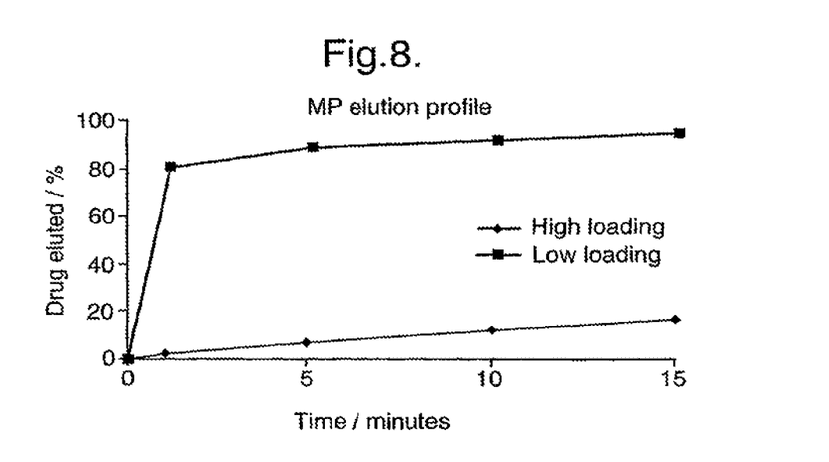
FIG. 8 shows MP elution profile.

FIG. 8 shows the 6α-methyl prednisolone elution profile for Example 7.

The present invention is illustrated in the accompanying examples:

REFERENCE EXAMPLE 1

Zwitterionic polymer coatings were investigated by allowing pyrene to diffuse into the polymer and studying the degree to which it is taken up, and the effects on the ratio of the fluorescence band intensities to see if there is any significant indication of the type of environment present.

Polymer coatings of interest were dissolved in an appropriate solvent (usually ethanol) at 20 mgml$^{-1}$. The solution was used to coat polymethylmethacrylate (PMMA) fluorescence cuvettes by simply pouring into the cuvette, draining, following by an oven curing at 70° C. overnight. Polymers studied were:

a) a copolymer of 2-methacryloyloxy ethyl-2'-trimethylammoniumethyl phosphate inner salt (MPC):n-butylmethacrylate:hydroxypropyl methacrylate (HPM):trimethoxysilylpropylmethacylate (TSM) 29:51:15:5 (by weight)

b) a copolymer of MPC:benzylacrylate:HPM:TSM 29:51:15:5 c) a copolymer of MPC:dodecylmethacrylate (DM):HPM:TSM: 45:35:15:5 d) a copolymer of MPC:DM:HPM:TSM: 29:51:15:5 e) a copolymer of MPC:DM:HPM:TSM: 15:65:15:5 f) poly(2-hydroxyethylmethacrylate).

The copolymers a-e were synthesised as disclosed in WO-A-9830615.

Analytical grade pyrene was used in high purity water (8.32×10$^{-4}$ M). The fluorescence spectrum was recorded using an excitation wavelength of 335 nm and scanned from 350-440 nm on a PE LS 50B Luminescence Spectrophotometer. Subtraction of the spectrum of each coating in water was necessary to remove the interference of a small band at 380 nm present in all methacrylate systems.

Environment information could be obtained by comparing the ratio of the intensity of the peaks at 373 nm (I1) and 383 nm (I3) (I3/I1). Where I3/I1 was similar for polymer systems, the comparative amount of pyrene present could be estimated by the maximum intensity of I1; alternatively, the entire peak area may offer an alternative measure of the comparative amount of pyrene present in different coatings. It was important to mark the side of the cuvette to ensure the same orientations was achieved each time it was replaced in the spectrophotometer.

FIG. 3A compares the fluorescence spectra of pyrene in lauryl methacrylate (dodecyl methacrylate) (8.32×10$^{-4}$ M) and water (8.32×10$^{-5}$ M). For water the I3/I1 ratio is 0.633 (literature value[1] 0.63) and the I3/I1 ratio for lauryl methacrylate is 1.029. This indicates the very different environments than might be expected to be seen within the polymer coating.

Pyrene solution added to the coated cuvettes was allowed to stand for 16 h, the cuvette emptied and washed thoroughly with ultrapure water, refilled with ultrapure water and the fluorescence spectrum recorded. The comparative maximum height of I1 was used to estimate the relative amounts of pyrene in the coatings. This was repeated for three cuvettes of each polymer and the average taken. Despite some variations between cuvettes, the trends were the same, indicating that the polymer formulations with more hydrophobic content seemed to contain more pyrene (FIG. 2). This is in contradiction to the water contents of these materials which vary in the opposite order. Hence for the varying systems, although water contents vary in the order c>d>f>e (88:40:38:27), the final fluorescence intensity (loading of pyrene achieved in the coating) varies according to e>d>c>f. This indicates that the pyrene is preferentially associating itself with hydrophobic areas within the coating.

The ratio of I3/I1 was also studied (FIG. 1) and again, those polymer with formal hydrophobic chains showed a greater ratio (indicating more hydrophobic environment for the pyrene). This polymer containing the benzyl side chain has a lower than expected I3/I1, initially indicating poor interaction with the pyrene. However, measurement of the I3/I1 for pyrene in the pure benzyl acrylate monomer showed that the maximum I3/I1 that could be expected would be 0.75 (i.e. less of a shift in fluorescent intensity is produced in this aromatic monomer compared to the lauryl monomer). PHEMA coating showed I3/I1 characteristic of pyrene in an aqueous environment (FIG. 3A), suggesting no formal hydrophobic domain exists.

REFERENCE EXAMPLE 2

Drug-Polymer Interaction versus Drug Solubility

There are examples of stent-based release of therapeutics that rely upon the poor solubility of the active agent in water to achieve a slow release rate, i.e. by relying for extended release of drug on poor solubility of the drug in water. When a graph of solubility versus release time (T90%) is plotted however, the relationship is extremely poor ($R^2$=0.006) indicating the solubility on its own does not account for the observed release characteristics.

This can be modelled further by comparing the theoretical release of drug into a known volume of water based purely upon its solubility and comparing this with its actual release profile from the polymer system into the same elution volume. Assuming that 100 μg of the drug is place on a surface, and that the drug is eluted off into 5 ml of solution, and then at various arbitrary points, 1 ml removed, and 1 ml of fresh solution added, the dissolution profiles for various drugs could be calculated and compared to experimental data obtained the same way. The variation between calculated and observed could be attributed to the interaction with the polymer matrix.

This is clearly illustrated by FIGS. 4a and b. Here, the theoretical release of dexamethasone (which has a log P where P is the partition coefficient between octanol and water of 2.55) and estradiol have been calculated and plotted on the graph (diamonds/circles) based on the solubility of the compound and the volume of water into which it is being eluted (Details of further loading and elution studies from polymer-coated stents are given below). The difference between this line and the observed data (squares) is the degree of interaction of the compound with the hydrophobic domains within the polymer coating which in this case is polymer d) from Ref. Example 1. It is the interaction that prolongs the release of the compound and offers some capability to control the delivery of the drug to its surrounding environment.

EXAMPLE 1

Estradiol Uptake Studies 1.1 Normal (Low) Loading Level 15 mm BiodivYsio DD stents provided with a cross-linked coating on both inner and outer walls of copolymer d) used in Reference Example 1 were provided with a coating of drug by immersing them in a 20 mg/ml solution of estradiol for 30 minutes, removing the stents from the solution and wick drying them on tissue then allowing them to dry for 2 hours at room temperature. The drug total loading was measured by HPLC, and found to be in the range 45-65 μg per stent.

1.2 High Loading Level 18 mm BiodivYsio stents premounted on their balloon delivery catheter were coated by dipping the balloon and stent in a volume of a 20 mg/ml solution of estradiol in ethanol for 5 minutes, removing and drying for 5 minutes, then pipetting 10 μl of the drug solution on to the stent/balloon and allowing to dry for 1 minute, this pipetting and drying step being repeated once, with a final 10 minute drying period. The balloons were inflated, deflated and the stents removed. The level of drug on each stent and balloon was determined using HPLC. The level of drug on the stents was in the range 225-250 μg per stent, and the amount on each balloon was about 190-220 μg.

1.3 High Loading Level Repeat

The method of example 1.2 was repeated with the stents premounted on either a 3 mm or 4 mm diameter balloon. For the 4 mm balloon system the mean level of drug was 240 with a range for 3 samples of 229-254 μg, giving an area distribution of 2.4 μg/mm$^2$ (range 2.3 to 2.6). For the 3 mm balloon system the mean loading per stent was 2.59 μg with a range for 5 samples of 243-276 μg. The area distribution is 2.6 μg/mm$^2$ (range 2.4-2.8).

EXAMPLE 2

Estradiol Elution Studies at 25° C.—Non-Flow System

Elution studies were carried out at 25° C. for upto 1 hour in gently agitated PBS. This was done by placing 15 mm DD stents loaded with estradiol, from Example 1.1 individually in vials containing 5 ml phosphate buffered saline (PBS) on rollers. At various time intervals up to 7 hours a 1 ml aliquot was removed and replaced with 1 ml fresh PBS. The stents and water aliquots were measured, to give the amount of drug eluted and the amount of drug remaining on the stents. The results are shown in FIG. 5. It may be seen that during the first hour estradiol was eluted relatively more quickly than the rest of the time and at 4 hours there was still 62% estradiol still remaining on the stent.

EXAMPLE 3

Release of 17β-Estradiol

The elution profile for 17β-estradiol, FIG. 6 from the stents produced in example 1.1, was assessed using an in-vitro test where five stents were vigorously stirred in a large volume (1000 ml) of PBS saline solution at 37° C. This test demonstrates that the stent is capable of a sustained release of 17β-estradiol over a duration of at least several hours. Aliquots of buffer were removed at various time points over a 24 hour period and analysed for 17β-estradiol content. The results are shown in FIG. 6. When translated into in-vivo conditions, the release profile is predicted to be over a prolonged period of time.

EXAMPLE 4

Estradiol Elution Studies in Flow-System

The elution of estradiol was examined in a flow system at 37° C. and evaluated over an 8 hour period. PBS was maintained at 37° C. in six stirred reservoirs (500 ml each) within a water bath. A length of silicone tubing (3 mm internal diameter) was attached from each reservoir to one of six stent chambers (4 mm internal diameter 80 mm long) and back to the respective reservoir via a peristaltic pump. The system was pumped using a flow rate of 100 ml/min to reach equilibrium temperature of 37° C. The flow was stopped and two estradiol loaded 15 mm stents loaded as in Example 1 were placed in each of the six stent chambers, and flow recommenced. A stent was then removed at various time periods and wick dried. These were used to measure the amount of estradiol remaining on the stent. The results are shown in FIG. 7. This shows that in this model the estradiol was eluted relatively more quickly than in the stirred 5 ml PBS of Example 2. Since the total volume of PBS passing over the stents in the flow model is 500 ml, it is likely that throughout the period the rate of desorption of drug from the stent was higher than the rate of absorption from the environment. This condition may not apply to the non-flow method.

EXAMPLE 5

In Vivo Test on Estradiol Loaded Stents

This study investigated the acute and short term effects of deploying estradiol (17β) loaded 18 mm stents produced generally as described in Example 1 above (ie loaded with drug whilst mounted on the balloon using either a single dipping step or the multi-step loading method) in porcine arteries. There were 3 arms to the study: 1) Control, using the non-drug-coated 18 mm BiodivYsio stent with the polymer coating d from the reference example 1, 2) low estradiol dose (about 45-65 μg per stent) using the dip only loading method of Example 1.1, and 3) high dose (about 225-250 μg per stent) by using the multi-step loading method (Ex. 1.2).

A total of 6 animals were each implanted with three stents, one each of the control, low and high dose, one stent in each of three coronary arteries. A balloon:artery ratio of about 1.25:1 (in the range (1.2-1.3):1) was used, the oversizing designed to cause an, injury to the artery wall resulting in neointimal formation resembling that occurring in stented human coronary arteries.

One month after implantation observations were made by quantitative coronary angiogram (QCA) of the mean lumen diameter (MLD). Subsequently the results were evaluated by histomorphometric analysis of intimal hyperplasia formation and vessel luminareas, as well as for the extent of re-endothelialisation. The results are shown in Table 1.

TABLE 1

|   | MLD mm | Intimal Area mm$^2$ (S.D.) | Luminal area mm$^2$ (S.D) |
|---|---|---|---|
| Control | 2.26 | 4.31 (1.1) | 3.49 (1.41) |
| Low | 2.31 | 3.60 (0.79) | 4.20 (1.74) |
| High | 2.53 | 2.54 (1.0) | 5.40 (1.70) |

The study showed a 40% reduction in intimal area in the 'High Dose' 17β-estradiol loaded stents compared with control stents (p<0.05), see FIG. 4. There was also a reduction in the Intimal Area/injury score ratio in the 'High Dose' 17β-estradiol group compared with the 'Control' stents (1.32±0.40 mm² vs 1.96.±−0.32 mm², for 17β-estradiol vs control respectively, P<0.01). There was no significant difference in the injury score for all three study arms.

A trend was noted for the Luminal Area where there was an increase in Luminal Area with an increase in dosage.

Re-endothelialization scores were high for all three study arms, suggesting that 17b-estradiol does not inhibit the healing process.

EXAMPLE 6α

Methylprednisolone Uptake Studies 6.1 Low Loading Level 15 mm BiodivYsio DD stents provided with a cross-linked coating on is both inner and outer walls of copolymer d) used in Reference Example 1 were provided with a coating of drug by immersing them in a 12.35 mg/ml solution of 6α-methyl prednisolone (MP) for 5 minutes, removing the stents from the solution and wick drying them on tissue then allowing them to dry for at least 1 hour at room temperature. The drug total loading was measured by placing the stent in ethanol (9.0 ml) and sonicated for 30 minutes. The concentration in the ethanol was determined by UV at 246.9 nm compared to standards. The loading was found to be in the range 30-40 μg per stent.

6.2 High Loading Level 18 mm BiodivYsio stents coated with the cross-linked polymer d) on both walls premounted on their balloon delivery catheter were coated by dipping the balloon and stent in a volume of a 12.0 mg/ml solution of MP in ethanol for 5 minutes, removing and drying for 5 minutes, then pipetting 10 μl of the drug solution on to the stent/balloon and allowing to dry for 1 minute, this pipetting and drying step being repeated thrice, with a final 10 minute drying period. The balloons were inflated, deflated and the stents removed. The level of drug on each stent was determined using the technique described above. The level of drug on the stents was in the range 250-300 μg per stent.

EXAMPLE 7

MP Elution Studies at 25° C.—Non Flow System

Elution studies were carried out at 25° C. for up to 1 hour in gently agitated PBS. This was done by placing 15 mm DD stents loaded with MP from Examples 6.1 and 6.2 individually in vials containing 5 ml phosphate buffered saline (PBS) on rollers. At various time intervals a 1 ml aliquot was removed and replaced with 1 ml fresh PBS. The stents and water aliquots were measured, to give the amount of drug eluted and the amount of drug remaining on the stents. The results are shown in FIG. 8.

EXAMPLE 6

In Vivo Test on MP and Dexamethasone Loaded Stents

This study investigated the acute and short term effects of deploying MP and dexamethasone loaded 18 mm stents produced generally as described in Example 1 above (i.e. loaded with drug whilst mounted on the balloon using either the single dipping step of example 1.1) or the multi-step loading method of example 1.2) in porcine arteries. There were 4 arms to the study: 1) Control, using the non-drug-coated 18 mm BiodivYsio DD stent (which is coated with polymer d), 2) low Dex dose (about 95 .mu.g per stent) using the dip only loading method, 3) high Dex dose (about 265 μg per stent) by using the multi-step loading method, and 4) high dose MP produced as described in Example 6.2 (about 270 μg per stent).

Stents were implanted into porcine arteries for 5 days, explanted, then assessed for inflammation by H&E staining and the results scored histopathologically and morphometrically on an arbitrary scale.

From nine measurements for each data point the following results were obtained: (p values in parentheses in table), 1=no difference, 0.05=95% confidence of a difference), see table 2.

TABLE 2

| Histopathological findings | | | | |
|---|---|---|---|---|
| | Inflammation | Injury | Thrombus | Perivaculitis |
| Control | 0.73 | 0.56 | 0.74 | 0.48 |
| +Dex Low dose | 0.73 | 0.53 | 0.77 | 0.51 |
| +Dex High dose | 0.57 | 0.40 | 0.54* | 0.45 |
| +MP | 0.51* | 0.42 | 0.50* | 0.39 |

| Morphometric Result | | | | |
|---|---|---|---|---|
| | Dia Sten (%) | Area Sten (%) | IEL Dia-Lum. Dia | EEL Dia-Lum. Dia |
| Control | 5 | 9 | 0.16 | 0.47 |
| +Dex Low dose | 4 (0.02) | 8 (0.14) | 0.14 (0.18) | 0.47 (1) |
| +Dex High dose | 4 (0.02) | 7 (0.005) | 0.13 (0.009) | 0.43 (0.24) |
| +MP | 3 (0) | 6 (0.001) | 0.11 (00 | 0.35 (0) |

*indicates statistically significant difference from control (p = 0.05)

The results of Examples 6 and 8 show that the high dose stents show a trend towards improved results.

EXAMPLE 9

Re-Endothelialisation of Dexamethasone-Loaded Stents

The dexamethasone-loaded stents (Low Dex) described in example 8 were implanted into porcine coronary arteries for 30 days. After this time the animals were sacrificed and the stented sections of the arteries removed and fixed. The vessel was cut longitudinally and opened out to expose the inner surface which was sputter coated and viewed under by SEM.

SEM revealed that the inner surface of the vessel had completely re-endothelialised over the stent struts.

EXAMPLE 10

Clinical Trial Assessment—30 Day Data for 71 Patients

Study of anti-restenosis with the BiodivYsio Dexamethasone eluting stent (STRIDE) which is a multi-centre prospective study performed at 7 centres in Belgium with 71 patients. The primary objective of this study was to evaluate the proportion of patients with binary restenosis 6 months after receiving a BiodivYsio stent loaded with dexamethasone i.e. produced by the same technique as the LowDex stent described in example 8. The secondary objectives were to evaluate the incidence of sub(acute) thrombosis to 30 days post procedure and the occurrence of MACE (death, recurrent myocardial infarction or clinically driven target lesion revascularisation) at 30 days and 6 months post procedure.

11, 15, 18 and 28 mm by 3.0 to 4.0 mm diameter BiodivYsio stents loaded with dexamethasone were under investigation. 30 day data for 71 patients (safety analysis set) are reported in this example. Other endpoints have not yet been reached and therefore will not be described.

71 patients (79% male) with an average height of 170 cm and weight of 79 Kg were enrolled into the study. 63% of patients had a history of hypercholesterolaemia and 69% had smoked or were current smokers. 47% of patients had multi-vessel disease and 44% had a history of previous MI. The vessels/lesions treated were in the following categories:

| Vessel | Treated | Lesion | Classification |
|---|---|---|---|
| RCA | 31% | A | 21% |
| LAD | 41% | B1 | 48% |
| Cx | 19% | B2 | 27% |
| Other | 9% | C | 4% |

The mean lesion length treated was 9 mm. The majority of patients had either a 15 mm (34%) or an 18 mm (39%) stent implanted.

At 30 day follow-up two patients had a MACE (1 patient died one day post procedure following coronary embolism and 1 patient had a non Q-wave MI) (Table 3). Three patients had serious adverse events that were unrelated to the study treatment Technical device success defined as intended stent successfully implanted as the first stent was 95%. Clinical device success defined as technical device success in the absence of MACE to discharge was achieved in 94% of patients.

The data presented in this initial interim analysis suggest that the presence of dexamethasone in the coating is not associated with an increased occurrence of MACE or serious adverse events and that the BiodivYsio Dexamethasone stent is safe in the short term for use in patients.

REFERENCE EXAMPLE 3

Assessment of Changing Solvent on DD Stent Delivery System

In order to load the pre-mounted (on a balloon delivery catheter (balloon formed from a nylon blend)) DD stent with non-water soluble drug, the stent/delivery system combination must be immersed in the drug solution. The aim of this experiment was to check if the solvent had a detrimental effect on the balloons. Pre-mounted BioDivYsio stents were placed in solvent for minutes then allowed to air dry to 5 minutes. The mechanical properties of the balloon were then assessed by a burst pressure test.

The samples were connected to a pressure pump and gauge and a positive pressure of 1 atm ($10^5$ Pa) applied and left for 30 seconds. The pressure was increased by 1 atm ($10^5$ Pa) every 30 seconds until the stent was fully deployed i.e. there were no creases or folds in the balloon.

The pressure was then increased to 16 atm which is the rated burst pressure for the balloon system, and held for 30 seconds. The pressure was then increased in 1 atm. steps and held for 30 seconds at each step, until the balloon burst. The results are in Table 2.

TABLE 3

Effect of Drug Loading Solvent on Balloon Burst Pressure

| Solvent | Deployment Pressure/atm. | Burst Pressure/atm. |
|---|---|---|
| None | 3 | >16 |
| Ethanol | 3 | >16 |
| Methanol | 3 | 23 ± 1 |
| DMSO | 3 | 24 ± 1 |

None of the solvents cause detrimental effects on the balloon. The choice of drug loading solvent is therefore related to drying rate and solvent toxicity, drug solubility, and swellability of the polymer.

The invention claimed is:

1. A method for producing a drug coated intravascular stent comprising the steps:
   a) coating a metallic stent body with a cross-linkable amphiphilic polymer;
   b) subjecting the cross-linkable amphiphilic polymer to conditions under which cross-linking takes place to produce a stent coated with polymer which, when swollen with water containing pyrene, has hydrophobic domains observable by pyrene fluorescence having an intensity ratio I3:I1 of at least 0.8;
   c) contacting at least the outer coated wall of the polymer coated stent with a liquid drug composition comprising a sparingly water-soluble restenosis inhibiting agent as the drug and an organic solvent in which the drug is at least partially dissolved and which is capable of swelling the cross-linked polymer of the coating, for a time sufficient to swell the polymer coating on the outer wall, to produce a wet drug-coated stent in which drug is present in an amount in the range of 20 μg to 1000 μg per stent;
   d) evaporating organic solvent from the wet stent to produce a dry drug-coated stent.

2. The method according to claim 1, wherein in step a), the metallic stent body is coated with the cross-linkable amphiphilic polymer on its inner wall or outer wall or both.

3. The method according to claim 1, wherein in step c), the drug is both absorbed into the polymer and adsorbed at the surface of the polymer coating, whereby, upon evaporation of the solvent in step d) crystals of drug are formed which are adherent to the surface of the dry-drug coated stent.

4. The method according to claim 1, wherein in step c) the contacting is by dipping the polymer coated stent in the liquid composition, optionally repeatedly.

5. The method according to claim 1, wherein in step c) the contacting includes flowing, spraying or dripping the liquid composition onto the stent and immediately allowing evaporation of solvent from the wet stent.

6. The method according to claim 1, wherein the stent is, between steps b) and c), mounted onto the stent delivery section of a delivery catheter, whereby the stent delivery section is also contacted with the said liquid drug composition.

7. The method according to claim 6, wherein the delivery catheter is a balloon catheter in which the balloon is formed of polyamide, and in which the organic solvent in the liquid drug composition is selected from the group consisting of dichloromethane, dimethylsulphoxide, $C_{1-4}$ alcohol and admixtures thereof.

8. The method according to claim 1, wherein the amphiphilic polymer comprises
   as the groups conferring hydrophobicity, pendant hydrophobic groups selected from $C_{4-24}$-alkyl, alkenyl and -alkynyl groups any of which is optionally substituted by one or more fluorine atoms, aryl, $C_{7-24}$ aralkyl, oligo ($C_{3-4}$ alkoxy) alkyl and siloxane groups, and
   as the groups conferring hydrophilicity, zwitterionic groups.

9. The method according to claim 8, wherein the polymer is formed from ethylenically unsaturated monomers including a zwitterionic monomer having said zwitterionic group, and a hydrophobic monomer having said hydrophobic group.

10. The method according to claim 9, wherein the ethylenically unsaturated monomers include one or more reactive monomers having a pendant reactive group capable of forming intermolecular crosslinks.

11. The method according to claim 8, wherein the zwitterionic monomer has the general formula I:

YBX      I wherein
B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;
X is a zwitterionic group; and
Y is an ethylenically unsaturated polymerisable group selected from $CH_2$=$C(R)CH_2O$—, $CH_2$=$C(R)CH_2OC(O)$—, $CH_2$=$C(R)OC(O)$—, $CH_2$=$C(R)O$—, $CH_2$=$C(R)CH_2OC(O)N(R^1)$—, $R^2OOCCR$=$CRC(O)O$—, $RCH$=$CHC(O)O$—, $RCH$=$C(COOR^2)CH_2C(O)O$—, wherein:
R is hydrogen or a $C_1$-$C_4$ alkyl group;
$R^1$ is hydrogen or a $C_1$-$C_4$ alkyl group or $R^1$ is —B-X where B and X are as defined above;
$R^2$ is hydrogen or a $C_{1-4}$ alkyl group;

A is —O— or —$NR^1$—;
K is a group —$(CH_2)_pOC(O)$—, —$(CH_2)_pC(O)O$—, —$(CH_2)_pOC(O)O$—, —$(CH_2)_pNR^3$—, —$(CH_2)_pNR^3C(O)$—, —$(CH_2)_pC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, or, optionally in combination with B, a valence bond,
p is from 1 to 12; and
$R^3$ is hydrogen or a $C_1$-$C_4$ alkyl group.

12. The method according to claim 11, wherein the cationic group in X is a quaternary ammonium group.

13. The method according to claim 11, wherein the anionic group in X is selected from sulphate, sulphonate, phosphate, phosphonate and carboxylate.

14. The method according to claim 11, wherein X is selected from groups of the general formula V:

in which the moieties $X^3$ and $X^4$, which are the same or different, are —O—, —S—, —NH— or a valence bond, and $W^+$ is a group comprising an ammonium, phosphonium or sulphonium cationic group and a group linking the anionic and cationic.

15. The method according to claim 9, wherein the hydrophobic monomer has the general formula VII $Y^1R^{13}$      VII wherein
$Y^1$ is selected from $CH_2$=$C(R^{14})CH_2O$—, $CH_2$=$C(R^{14})CH_2OC(O)$—, $CH_2$=$C(R^{14})OC(O)$—, $CH_2$=$C(R^{14})O$—, $CH_2$=$C(R^{14})CH_2OC(O)N(R^{15})$—, $R^{16}OOCCR^{14}$=$CR^{14}C(O)O$—, $R^{14}CH$=$CHC(O)O$—, $R^{14}CH$=$C(COOR^{16})CH_2C(O)O$—, wherein:
$R^{14}$ is hydrogen or a $C_1$-$C_4$ alkyl group;
$R^{15}$ is hydrogen or a $C_1$-$C_4$ alkyl group or $R^{15}$ is $R^{13}$;
$R^{16}$ is hydrogen or a $C_{1-4}$ alkyl group;
$A^1$ is —O— or —$NR^{15}$—;
$K^1$ is a group —$(CH_2)_qOC(O)$—, —$(CH_2)_qC(O)O$—, —$(CH_2)_qOC(O)O$—, —$(CH_2)_q(NR^{17})$—, —$(CH_2)_qNR^{17}C(O)$—, —$(CH_2)_qC(O)NR^{17}$—, —$(CH_2)_qNR^{17}C(O)O$—, —$(CH_2)_qOC(O)NR^{17}$—, —$(CH_2)_gNR^{17}C(O)$ NR$^{17}$— (in which the groups R$^{17}$ are the same or different), —(CH$_2$)$_q$O—, —(CH$_2$)$_q$SO$_3$—, or a valence bond, p is from 1 to 12;

R$^{17}$ is hydrogen or a C$_1$-C$_4$ alkyl group; and

R$^{13}$ is the hydrophobic group.

16. The stent according to claim 15, wherein R$^{13}$ is selected from
   a) C$_{4-16}$ alkyl groups;
   b) aryl and aralkyl; and
   c) a siloxane group —(CR$^{18}_2$)$_{qq}$(SiR$^{19}_2$)(OSiR$^{19}_2$)$_{pp}$R$^{19}$ in which each group R$^{18}$ is the same or different and is hydrogen or alkyl of 1 to 4 carbon atoms, or aralkyl, for example benzyl or phenethyl, each group R$^{19}$ is alkyl of 1 to 4 carbon atoms, qq is from 1 to 6 and pp is from 0 to 49.

17. The method according to claim 10, wherein the each reactive monomer has the general formula VIII $$Y^2B^2R^{20} \qquad \text{VIII}$$

wherein

B$^2$ is a straight or branched alkylene, oxaalkylene or oligo-oxaalkylene chain optionally containing one or more fluorine atoms up to and including perfluorinated chains, or B$^2$ is a valence bond;

Y$^2$ is an ethylenically unsaturated polymerisable group selected from

CH$_2$=C(R$^{21}$)CH$_2$—O—, CH$_2$=C(R$^{21}$)CH$_2$OC(O)—, CH$_2$=C(R$^{21}$)OC(O)—, CH$_2$=C(R$^{21}$)O—, CH$_2$=C(R$^{21}$)CH$_2$OC(O)N(R$^{22}$)—, R$^{23}$OOCCR$^{21}$=CR$^{21}$C(O)O—, R$^{21}$H=CHC(O)O—, R$^{21}$H=C(COOR$^{23}$)CH$_2$C(O)O— where

R$^{21}$ is hydrogen or C$_1$-C$_4$ alkyl;

R$^{23}$ is hydrogen, or a C$_{1-4}$-alkyl group;

A$^2$ is —O— or —NR$^{22}$—;

R$^{22}$ is hydrogen or a C$_1$-C$_4$ alkyl group or R$^{22}$ is a group B$^2$R$^{20}$;

K$^2$ is a group —(CH$_2$)$_k$OC(O)—, (CH)$_k$C(O)O—, —(CH$_2$)$_k$OC(O)O—, —(CH$_2$)$_k$NR$^{22}$—, —(CH$_2$)$_k$NR$^{22}$C(O)—, —(CH$_2$)$_k$OC(O)O—, —(CH$_2$)$_k$NR$^{22}$—, —(CH$_2$)$_k$NR$^{22}$C(O)—, —(CH$_2$)$_k$C(O)NR$^{22}$—, —(CH$_2$)$_k$NR$^{22}$C(O)O—, CH$_2$)$_k$OC(O)NR$^{22}$—, —(CH$_2$)$_k$NR$^{22}$C(O)NR$^{22}$— (in which the groups R$^{22}$ are the same or different), —(CH$_2$)$_k$O—, —(CH$_2$)$_k$SO$_3$—, a valence bond and k is from 1 to 12; and R$^{20}$ is a cross-linkable group.

18. The method according to claim 17, wherein R$^{20}$ is selected from the group consisting of ethylenically and acetylenically unsaturated group containing radicals, aldehyde groups, silane and siloxane groups containing one or more substituents selected from halogen atoms and C$_{1-4}$-alkoxy group, hydroxyl, amino, carboxyl, epoxy, —CHOHCH$_2$Hal (in which Hal is selected from chlorine, bromine and iodine atoms), succinimido, tosylate, triflate, imidazole carbonyl amino, optionally substituted triazine groups, acetoxy, mesylate, carbonyl di(cyclo)alkyl carbodiimidoyl, isocyanate, acetoacetoxy, and aximino.

19. The method according to claim 18, wherein R$^{20}$ comprises a silane group containing at least one substituent selected from halogen atoms and C$_{1-4}$-alkoxy groups.

20. The method according to claim 18, wherein R$^{20}$ comprises a silane group containing at least three methoxy groups.

* * * * *